United States Patent
Qian et al.

(10) Patent No.: US 12,075,863 B2
(45) Date of Patent: Sep. 3, 2024

(54) MASK WITH STERILIZATION FUNCTION

(71) Applicant: Beijing FUNATE Innovation Technology Co., LTD., Beijing (CN)

(72) Inventors: Li Qian, Beijing (CN); Yu-Quan Wang, Beijing (CN); Li Fan, Beijing (CN)

(73) Assignee: Beijing FUNATE Innovation Technology Co., LTD., Beijing (CN)

( * ) Notice: Subject to any disclaimer, the term of this patent is extended or adjusted under 35 U.S.C. 154(b) by 863 days.

(21) Appl. No.: 17/079,166

(22) Filed: Oct. 23, 2020

(65) Prior Publication Data

US 2022/0015470 A1 Jan. 20, 2022

(30) Foreign Application Priority Data

Jul. 17, 2020 (CN) .......................... 202010690234.9

(51) Int. Cl.
*A41D 13/11* (2006.01)
*A61L 2/03* (2006.01)
(Continued)

(52) U.S. Cl.
CPC ............ *A41D 13/1161* (2013.01); *A61L 2/03* (2013.01); *A61L 2/26* (2013.01); *A61L 9/16* (2013.01);
(Continued)

(58) Field of Classification Search
CPC ... A62B 18/084; A62B 18/025; A62B 23/025; C01B 2202/02; C01B 2202/08; C01B 2202/06; A41D 13/1161; A41D 13/1192; A41D 13/11; A41D 27/28; A41D 31/145; B32B 29/002; B32B 5/26; B01D 46/546; B01D 39/2065; B01D 39/2055; B01D 39/2041; B01D 2239/065; B01D 2239/025; B01J 20/205; A61L 2/03; A61L 2/26; A61L 9/16; A61L 2209/14; A61L 2209/20; A61L 2202/26; A61L 2/04
See application file for complete search history.

(56) References Cited

U.S. PATENT DOCUMENTS 4,045,338 A * 8/1977 Miyamoto ............... B01J 39/24
  210/679
10,322,303 B2 6/2019 Qian et al.
(Continued)

FOREIGN PATENT DOCUMENTS

CN 101623134 1/2010
CN 202190779 4/2012
(Continued)

*Primary Examiner* — Ophelia A Hawthorne
(74) *Attorney, Agent, or Firm* — ScienBiziP, P.C.

(57) ABSTRACT

A mask with sterilization function is provided. The mask comprises two straps, a mask body, a functional layer, a first electrode, a second electrode, and a power inlet. The functional layer, the first electrode and the second electrode located in the mask body. The first electrode and the second electrode are located on a surface of the functional layer and are electrically connected to the power inlet. The first electrode and the second electrode are configured to input a current to the functional layer to heat the functional layer. The functional layer is a conductive layer and comprises a plurality of micropores.

14 Claims, 10 Drawing Sheets

(51) Int. Cl.
    *A61L 2/26*         (2006.01)
    *A61L 9/16*         (2006.01)

(52) U.S. Cl.
    CPC ....... *A61L 2209/14* (2013.01); *A61L 2209/20* (2013.01)

(56) References Cited

U.S. PATENT DOCUMENTS

| | | | |
|---|---|---|---|
| 2016/0015098 A1* | 1/2016 | Conlon | A41D 13/1115 29/428 |
| 2017/0209719 A1 | 7/2017 | Tang | |
| 2021/0321703 A1* | 10/2021 | Bystricky | B32B 5/022 |

FOREIGN PATENT DOCUMENTS

| | | |
|---|---|---|
| CN | 204146394 | 2/2015 |
| CN | 111227359 | 6/2020 |
| JP | 3152585 | 8/2009 |
| JP | 2018-107116 | 7/2018 |
| TW | M409079 | 8/2011 |
| TW | M510761 | 10/2015 |

\* cited by examiner

MASK WITH STERILIZATION FUNCTION

CROSS-REFERENCE TO RELATED APPLICATIONS

The application is also related to co-pending applications entitled, "MASK WITH STERILIZATION FUNCTION", filed on Oct. 23, 2020, with file Ser. No. 17/079179.

FIELD

The subject matter herein generally relates to a mask with sterilization function.

BACKGROUND

Currently in the epidemic period of new coronary pneumonia, the demand for masks is huge. The masks currently used are all disposable masks, which are not economical and environmentally friendly. Moreover, users wearing disposable masks in public places, if the surface of the mask is contaminated by the new crown virus, in addition to being unable to wear it again, after the mask is discarded, the new crown virus on the mask will still exist, which will pollute the environment and may cause cross infection, which is not conducive to Control of the epidemic.

BRIEF DESCRIPTION OF THE DRAWINGS

Implementations of the present technology will now be described, by way of embodiments, with reference to the attached figures, wherein.

DETAILED DESCRIPTION

The disclosure is illustrated by way of example and not by way of limitation in the figures of the accompanying drawings in which like references indicate similar elements. It should be noted that references to "another," "an," or "one" embodiment in this disclosure are not necessarily to the same embodiment, and such references mean "at least one."

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

Several definitions that apply throughout this disclosure will now be presented.

The term "contact" is defined as direct and physical contact. The term "substantially" is defined to be that while essentially conforming to the particular dimension, shape, or other feature that is described, the component is not or need not be exactly conforming to the description. The term "comprising," when utilized, means "including, but not necessarily limited to"; it specifically indicates open-ended inclusion or membership in the so-described combination, group, series, and the like.

Figure 1:
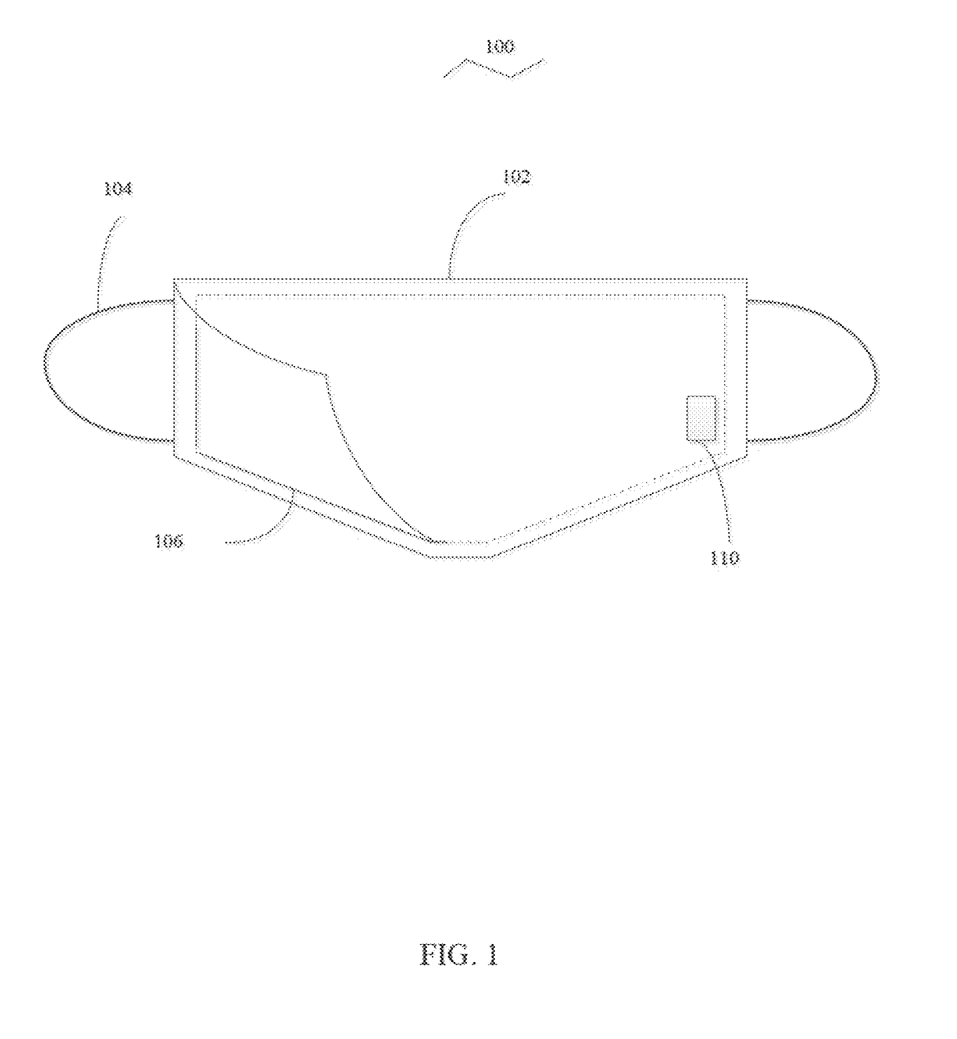
FIG. 1 is a sectional schematic view of a mask with sterilization function according to a first embodiment.
Figure 2:
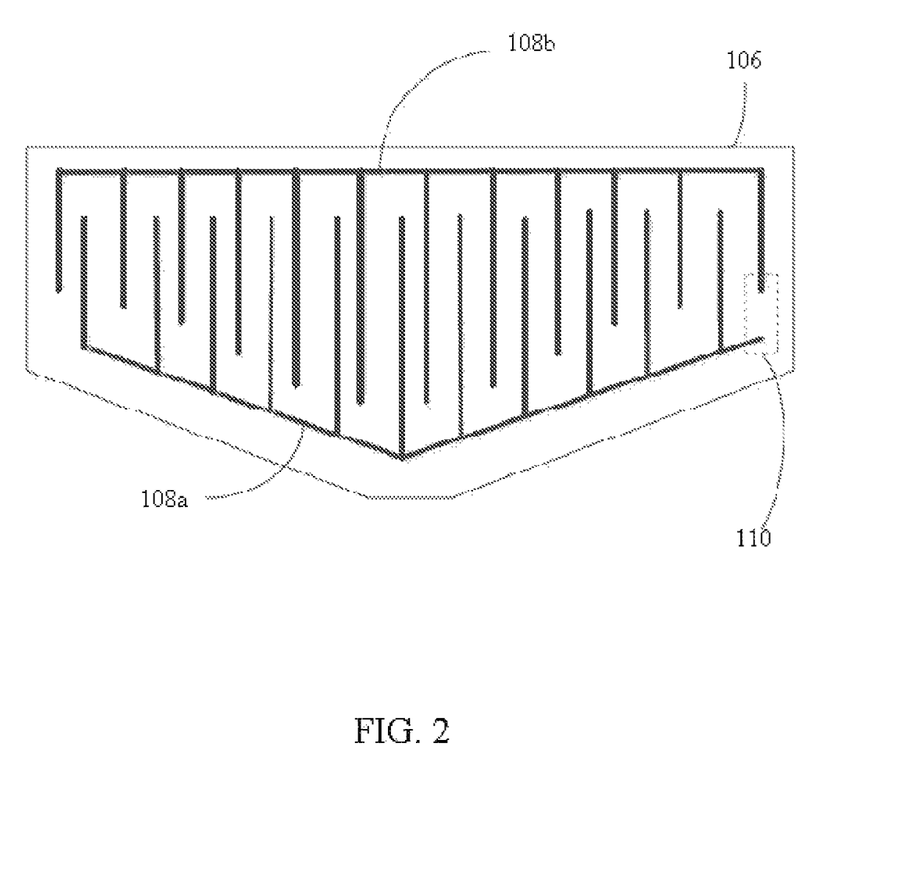
FIG. 2 is a schematic view of an internal structure of the mask with sterilization function in FIG. 1.

Referring to FIGS. 1 and 2, a mask with sterilization function 10 according to a first embodiment is provided. The mask with sterilization function 10 includes a mask body 102, two straps 104, a functional layer 106, a first electrode 108a, a second electrode 108b and a power inlet 110. The functional layer 106 and the two electrodes 108a and 108b are located in the mask body 102, and the two electrodes 108a and 108b are located on a surface of the functional layer 106 and are electrically connected to the power inlet 110. The two electrodes 108a, 108b are used to input current to the functional layer 106 to heat the functional layer 106. The functional layer 106 includes a plurality of micropores, which is a carbon nanotube layer or a carbon fiber layer.

The mask body 102 comprises at least two layers, an inner layer and an outer layer. The functional layer 106 is located between the inner layer and the outer layer. The two straps 104 are respectively arranged on opposite ends of the mask body 102. The two straps 104 are respectively arranged on two sides of the mask body 102 for hanging the mask on a user's ears. It can be understood that the two straps 104 can also be arranged in other ways, such as a sleeve type.

A material of the mask body 102 is preferably a light, thin and air-permeable material, which can be cotton, silk, gauze, non-woven fabric, hemp, fiber, nylon, spandex, polyester or polyacrylonitrile, etc. Preferably, the material of the mask body 102 is an air negative ion modified material. The air anions in the air anion modified material can reduce the activity of microorganisms and germs in the air, thereby inhibiting the survival of microorganisms or germs in the mask. At the same time, it can neutralize the positive ion-carrying dust, aerosol and other polluting particles in the air to achieve the purpose of purifying the air.

The mask body 102 is a two-layer structure. The mask body 102 is not limited to the two-layer structure in this embodiment and may also be a multi-layer structure. The mask body 102 can be an integrally formed structure or can be formed by combining at least two layers of structures by sewing or bonding. It can be understood that sizes of the at least two layers structure can be the same or different, as long as it is ensured that the at least two layers structure can comprise an accommodation space for placing the functional layer 106. The shape of the mask body 102 can be arc, semi-circular, cup, rectangle or other desired shapes.

Preferably, the straps 104 are elastic. The arrangement of the strap 104 is not limited to this embodiment, as long as it can fix the mask with the sterilization function 100 on the user's face. For example, only one strap 104 can be provided. Two ends of the strap 104 are respectively located on the two sides of the mask body 102. The strap 104 can fix the mask with the sterilization function 100 on the back of the user's head. It can be understood that, the mask with the sterilization function 100 can have no straps in some embodiment. For example, a re-adhesive sticking piece is directly arranged on the inner surface of the mask body 102, and the sticking piece can be directly stuck to the skin so it will not cause pressure to the user and will not hinder the blood capillaries. The comfort of the user is greatly improved.

The functional layer 106 can be a filter layer and a heating sterilization layer. A thickness and a shape of the functional layer 106 can be designed according to actual needs. The functional layer 106 is a flexible layer including a plurality of micropores. Diameters of the micropores can be greater than 1 micrometer. The diameters of the micropores can be greater than 1 micrometer and less than 5 micrometers. Preferably, the diameters of the micropores can be in a range from 1 micrometer and to 2.5 micrometers. The functional layer 106 is a conductive layer. When a voltage is applied to the functional layer 106, a current is generated in the functional layer 106, thereby generating Joule heat and increasing the temperature of the functional layer 106.

Figure 3:
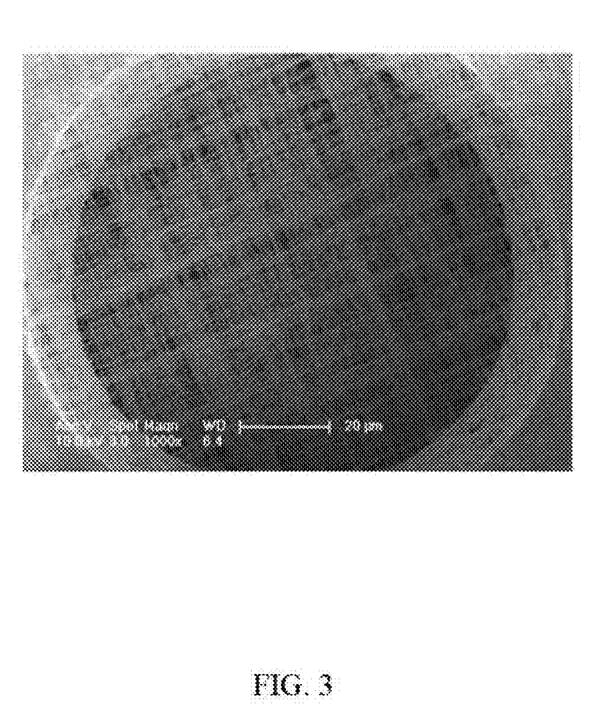
FIG. 3 shows a Scanning Electron Microscope (SEM) image of a carbon nanotube layer.
Figure 4:
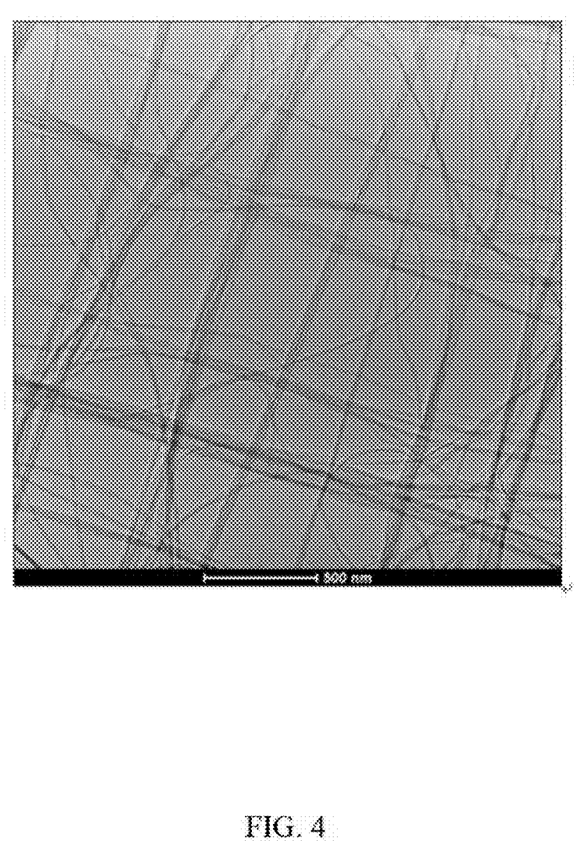
FIG. 4 shows a Transmission Electron Microscope (TEM) image of the carbon nanotube layer.

The functional layer 106 can be a carbon nanotube layer. Referring to FIGS. 3 and 4, the carbon nanotube layer includes a plurality of carbon nanotubes joined by van der Waals attractive force therebetween. The carbon nanotube layer can be a substantially pure structure of carbon nanotubes, with few impurities. The carbon nanotube layer can be a freestanding structure so that the carbon nanotube layer can be supported by itself without a substrate. For example, if at least one point of the carbon nanotube layer is held, the entire carbon nanotube layer can be lifted while retaining its structural integrity.

The carbon nanotubes in the carbon nanotube layer can be orderly or disorderly arranged. The term 'disordered carbon nanotube layer' refers to a structure where the carbon nanotubes are arranged along different directions, and the aligning directions of the carbon nanotubes are random. The number of carbon nanotubes arranged along each different direction can be almost the same (e.g. uniformly disordered). The disordered carbon nanotube layer can be isotropic, namely, the carbon nanotube layer has properties identical in all directions of the carbon nanotube layer. The carbon nanotubes in the disordered carbon nanotube layer can be entangled with each other.

The carbon nanotube layer including ordered carbon nanotubes is an ordered carbon nanotube layer. The term 'ordered carbon nanotube layer' refers to a structure where the carbon nanotubes are arranged in a consistently systematic manner, e.g., the carbon nanotubes are arranged approximately along a same direction and/or have two or more sections within each of which the carbon nanotubes are arranged approximately along a same direction (different sections can have different directions). The carbon nanotubes in the carbon nanotube layer can be selected from single-walled, double-walled, and/or multi-walled carbon nanotubes. The carbon nanotube layer may include at least one carbon nanotube film. In other embodiments, the carbon nanotube layer is composed of one carbon nanotube film or at least two carbon nanotube films. In other embodiments, the carbon nanotube layer consists of one carbon nanotube film or at least two carbon nanotube films.

Figure 5:
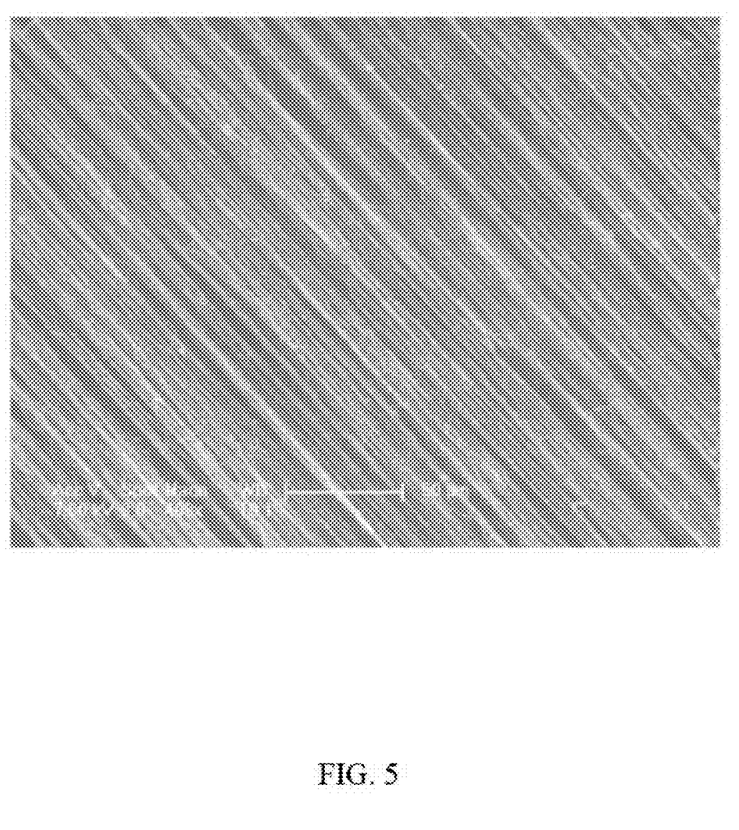
FIG. 5 shows an SEM image of a drawn carbon nanotube film.
Figure 6:
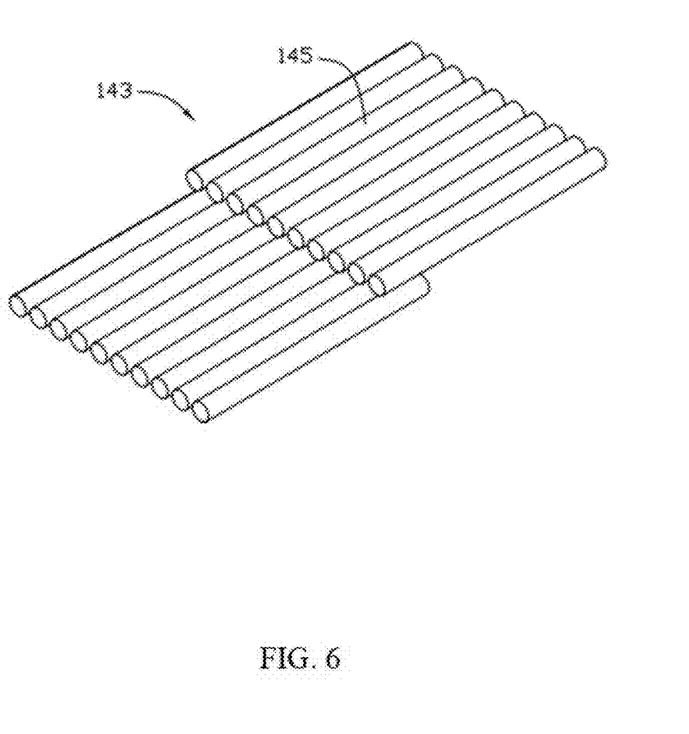
FIG. 6 is a schematic view of carbon nanotube segments in the drawn carbon nanotube film.

In one embodiment, the carbon nanotube film can be a drawn carbon nanotube film. Referring to FIG. 5, the drawn carbon nanotube film includes a number of successive and oriented carbon nanotubes joined end-to-end by van der Waals attractive force therebetween. The drawn carbon nanotube film is a freestanding film. Each drawn carbon nanotube film includes a number of successively oriented carbon nanotube segments joined end-to-end by van der Waals attractive force therebetween. Referring to FIG. 6, each carbon nanotube segment 143 includes a number of carbon nanotubes 145 substantially parallel to each other and joined by van der Waals attractive force therebetween. Some variations can occur in the drawn carbon nanotube film. The carbon nanotubes in the drawn carbon nanotube film are oriented along a preferred orientation. The drawn carbon nanotube film can be treated with an organic solvent to increase the mechanical strength and toughness of the drawn carbon nanotube film and reduce the coefficient of friction of the drawn carbon nanotube film. A thickness of the drawn carbon nanotube film may range from about 0.5 nanometers to about 100 micrometers. The drawn carbon nanotube film can be used as a carbon nanotube layer directly.

The carbon nanotubes in the drawn carbon nanotube film can be single-walled, double-walled, and/or multi-walled carbon nanotubes. The diameters of the single-walled carbon nanotubes may range from about 0.5 nanometers to about 50 nanometers. The diameters of the double-walled carbon nanotubes may range from about 1 nanometer to about 50 nanometers. The diameters of the multi-walled carbon nanotubes may range from about 1.5 nanometers to about 50 nanometers. The lengths of the carbon nanotubes may range from about 200 micrometers to about 900 micrometers.

The carbon nanotube layer may include at least two stacked drawn carbon nanotube films. The carbon nanotubes in the drawn carbon nanotube film are aligned along one preferred orientation. An angle can exist between the orientations of carbon nanotubes in adjacent drawn carbon nanotube films, whether stacked or adjacent. An angle between the aligned directions of the carbon nanotubes in two adjacent drawn carbon nanotube films may range from approximately 0 degrees to approximately 90 degrees (e.g. about 15 degrees, 45 degrees, or 60 degrees).

Figure 7:
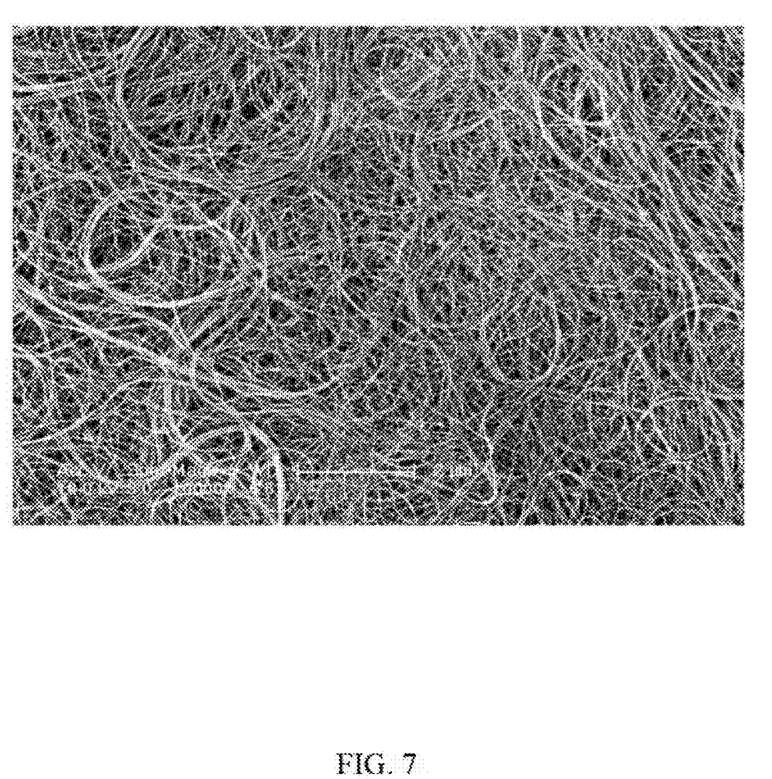
FIG. 7 shows an SEM image of a flocculated carbon nanotube film.

In other embodiments, the carbon nanotube film can be a flocculated carbon nanotube film. Referring to FIG. 7, the flocculated carbon nanotube film may include a plurality of long, curved, and disordered carbon nanotubes entangled with each other. Furthermore, the flocculated carbon nanotube film can be isotropic. The carbon nanotubes can be substantially uniformly dispersed in the flocculated carbon nanotube film. Adjacent carbon nanotubes are acted upon by van der Waals attractive force to obtain an entangled structure with micropores defined therein. Because the carbon nanotubes in the flocculated carbon nanotube film are entangled with each other, the carbon nanotube layer employing the flocculated carbon nanotube film has excellent durability and can be fashioned into desired shapes with a low risk to the integrity of the carbon nanotube layer. A thickness of the flocculated carbon nanotube film may range from about 0.5 nanometers to about 1 millimeter.

Figure 8:
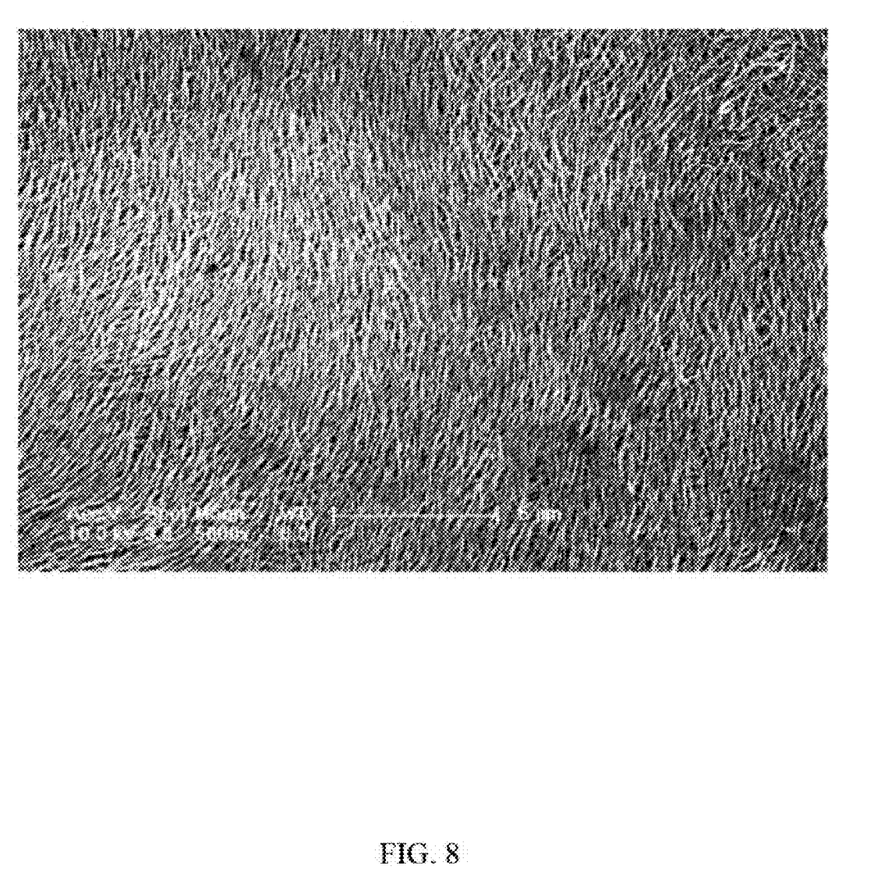
FIG. 8 shows an SEM image of a pressed carbon nanotube film.

Referring to FIG. 8, in other embodiments, the carbon nanotube film can be a pressed carbon nanotube film. The pressed carbon nanotube film is formed by pressing a carbon nanotube array. The carbon nanotubes in the pressed carbon nanotube film are arranged in a same direction different directions. The carbon nanotubes in the pressed carbon nanotube film can rest upon each other. Adjacent carbon nanotubes are attracted to each other and are joined by van der Waals attractive force. An angle between a primary alignment direction of the carbon nanotubes and a surface of the pressed carbon nanotube film is in a range from 0 degrees to 15 degrees. The greater the pressure applied, the smaller the angle obtained. In one embodiment, the carbon nanotubes in the pressed carbon nanotube film are arranged along different directions, the carbon nanotube layer can be isotropic. A thickness of the pressed carbon nanotube film may range from about 0.5 nanometers to about 1 millimeter.

In the first embodiment, the carbon nanotube layer consists of four layers of drawn carbon nanotube films, and a cross angle of adjacent drawn carbon nanotube films is 90 degrees, and the diameter of the micropores in the carbon nanotube layer is 1.5 micrometers.

In other embodiments, the functional layer can be a carbon fiber layer. The carbon fiber layer includes a plurality of carbon fibers located randomly and entangled with each other.

The mask with sterilization function 100 provided by this embodiment of uses the carbon nanotube layer as a functional layer. The carbon nanotubes are lighter in weight and have better flexibility. Therefore, the mask with sterilization function 100 is light in weight and thin in thickness. Because the carbon nanotubes have large specific surface areas of 170 $m^2/g$, they have a good adsorption effect on toxic gases in the air. The mask with sterilization function of the present invention does not require additional adsorption layer and can achieve the purpose of further purifying the air. In addition, since the carbon nanotubes are relatively pure, the carbon nanotube film including the plurality of carbon nanotubes have a greater viscosity and can be adhered to the mask body well without using an adhesive. In addition, its viscosity is relatively high, and it can also adhere to some impurities such as dust that are difficult to filter, which can achieve the purpose of further purifying the air.

The functional layer 106 can be a carbon fiber layer comprising a plurality of carbon fibers overlapped with each other. A length of the carbon nanotube fiber can be greater than 100 micrometers. The carbon fibers are arranged randomly. A plurality of micropores are formed in the carbon fiber layer.

The first electrode 108a and the second electrode 108b are respectively located at two ends of the functional layer 106 and are arranged on the surface of the functional layer 106. In this embodiment, the first electrode 108a and the second electrode 108b are cross-finger electrodes. The first electrode 108a or the second electrode 108b includes a horizontal wire and a plurality of vertical wires, where each of the vertical wires is parallel and spaced apart. One end of each vertical wire is connected to the horizontal wire, and the other end extends outward from the horizontal wire. The horizontal wire and the vertical wire can be perpendicular to each other. The horizontal wires are substantially flush with one side of the functional layer 106. The horizontal wires of the first electrode 108a and the second electrode 108b can be parallel to each other or arranged at a certain angle. The vertical wires of the first electrode 108a and the second electrode 108b are alternately arranged, spaced apart from each other and parallel with each other. One ends of the horizontal wires of the first electrode 108a and the second electrode 108b are electrically connected to the power inlet 110, and an external power source is energized to the first electrode 108a and the second electrode 108b through the power inlet 110. Preferably, a distance between one vertical wire of the first electrode 108a and one vertical wire of the second electrode 108b adjacent with each other can be in a range from 1 millimeter to 10 millimeters. In this embodiment, the distance between the adjacent vertical wires is 2 mm. If the temperature inside the mask body 102 needs to reach 56 degrees, then the input voltage will be at 5 V, the current at 1 A, and the power at 5 W. It can be understood that the input power, input voltage, and current of the power supply are not only related to a distance between the vertical wires, but also related to other parameters of the mask with sterilization function, such as the thickness of the mask with sterilization function and the temperature at which the mask with sterilization function needs to be heated. Therefore, the input power, input voltage and current of the power supply can be adjusted according to actual conditions. Preferably, the input power of the power supply is 3-10 watts, the voltage is 3-10 volts, and the voltage is 0.5-2 A.

A material of the first electrode 108a and the second electrode 108b can be metal, alloy, indium tin oxide (ITO), antimony tin oxide (ATO), conductive silver paste, conductive polymer, conductive carbon nanotube, etc. The metal or alloy material can be aluminum, copper, tungsten, molybdenum, gold, titanium, neodymium, palladium, cesium or any combination of alloys. In this embodiment, the first electrode 108a and the second electrode 108b are both linear copper conductive films with a thickness of 1 micron. The first electrode 108a and the second electrode 108b should be made of materials with better flexibility and small thickness.

The mask with sterilization function 100 can further include a support, which is arranged in the mask body so that the mask body can have a larger cavity used to expand the effective flow area, thereby reducing the wearer's breathing resistance. A material of the support can be plastic, metal, or the like.

The power inlet 110 of the mask with sterilization function 100 can be electrically connected to any external power source. Optionally, the mask with sterilization function 100 can further have a dedicated power source (not shown). And the power source includes power adjustment buttons. The power adjustment buttons include a high gear and a low gear. When in the high gear, the power source input an electrical signal with a higher power to the first electrode 108a and the second electrode 108b, and the temperature of the functional layer 106 is higher, which can achieve higher temperatures inside and outside the mask, and kill bacteria and viruses located inside and outside of the mask body. When in the low gear, the power source input an electrical signal with lower power to the first electrode 108a and the second electrode 108b, and the temperature of the functional layer 106 is lower than the temperature of the functional layer 106 at the high gear. As such, the temperature outside of the mask is low, but at the same time, the temperature inside the mask body is high enough to kill bacteria and viruses inside the mask body. Due to the low temperature outside the mask, users can wear the mask with sterilization function 100 while the mask with sterilization function 100 is turn on the power.

The mask with sterilization function 100 can be self-heated for sterilization after being used for a certain period of time, or after the user entering and exiting a confined space that may be contaminated by viruses. That is, an electrical signal is applied between the first electrode 108a and the second electrode 108 through the power inlet 110, and the functional layer 106 between the vertical wires of the first electrode 108a and the second electrode 108b is in a conductive state. There is a current flowing through adjacent wires and the functional layer 106 between the adjacent vertical wires, and the functional layer 106 generates Joule heat and the temperature of the functional layer 106 rises. The functional layer 106 heats the mask body 102 to achieve the effect of sterilization and purification, so that the mask with the sterilization function 100 can be used repeatedly. Since the functional layer 106 includes a plurality of micropores, the functional layer 106 has good air permeability and can also filter pollutant particles in the air. The functional layer 106 is a large-area layered structure that can cover the entire lateral area of the mask. A temperature of the functional layer 106 is almost the same in the whole surface of the functional layer 106. Therefore, the inside of the mask can be heated quickly without causing local overheating of the mask, and when heating and sterilizing, the temperature outside or inside the mask is uniform.

Compared with a conventional mask by adding metal wires to the mask to heat and sterilize the mask, the mask with a sterilization function provided by the present invention has significant advantages. For a conventional mask that is heated and sterilized by metal wires, the metal wires are very slim to improve the flexibility of the metal. To ensure the breathability of the conventional mask, the metal wires cannot cover the entire mask in a large area, and there is a large gap between the metal wires. During the heating process, the heat of the metal wires is transferred to the mask body. For the entire mask to reach a sterilization temperature, the local temperature of each metal wire needs to be 5-15 degrees higher than the sterilization temperature to make the internal temperature of the entire mask reach the sterilization temperature. In addition, the temperature of each metal wire needs to be 15-25 degrees higher than sterilization temperature. The higher temperature of the metal wires is, the more heating power is required. This will cause the part of the mask that is in direct contact with the metal wires to be too hot, which may cause the mask to ignite spontaneously or burn the user during the heating and sterilization process. Therefore, this kind of mask heated by metal wires has a greater safety hazard. For example, if a temperature to deactivate new coronavirus is about 56 degrees, the temperature of the metal wire will need to reach 66 degrees or higher to keep a minimum temperature inside the mask at 56 degrees, and the temperature of the metal wire will need to reach 80 degrees or higher to keep a minimum temperature outside the mask at 56 degrees. That way, the local temperature of the mask is too high. However, for the mask with sterilization function provided by the present invention, if the internal temperature of the mask needs to reach the sterilization temperature of about 56 degrees, the temperature inside the mask will only need to be at 56 degrees. That is because the area of the functional layer covers most of the mask area, and the temperature of the functional layer only needs to reach 56 degrees or slightly higher than 56 degrees. When the internal temperature is 56 degrees, the temperature outside the mask is below 40 degrees. The user can wear the mask while heating and sterilizing, keeping the mask clean at all times. To remove bacteria and viruses outside of the mask, the temperature of the functional layer needs to be just higher than 70 degrees to achieve the lowest temperature outside the mask 56 degrees, since the area of the functional layer covers most of the area of the mask. Therefore, there is no safety hazard.

Figure 9:
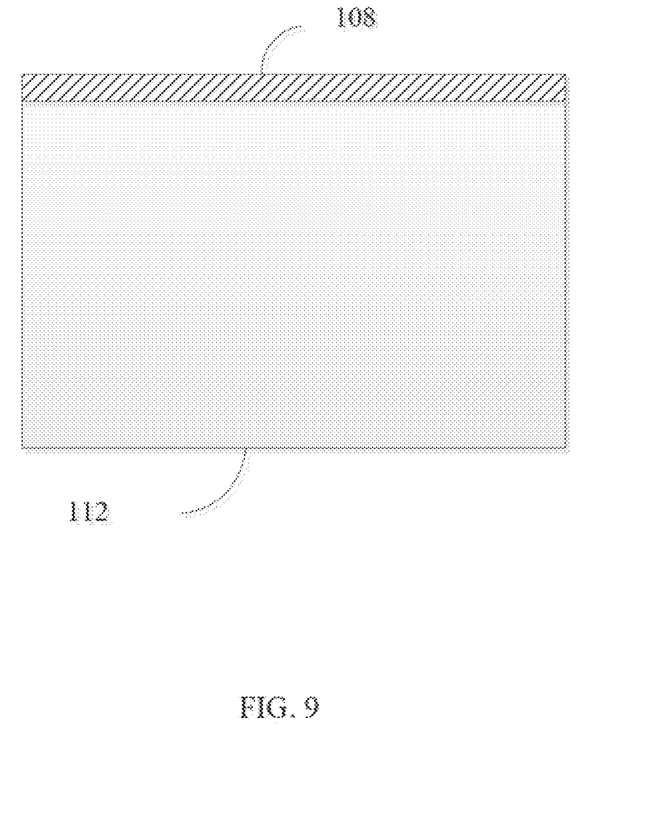
FIG. 9 is a schematic view of a mask with sterilization function according to a second embodiment.
Figure 10:
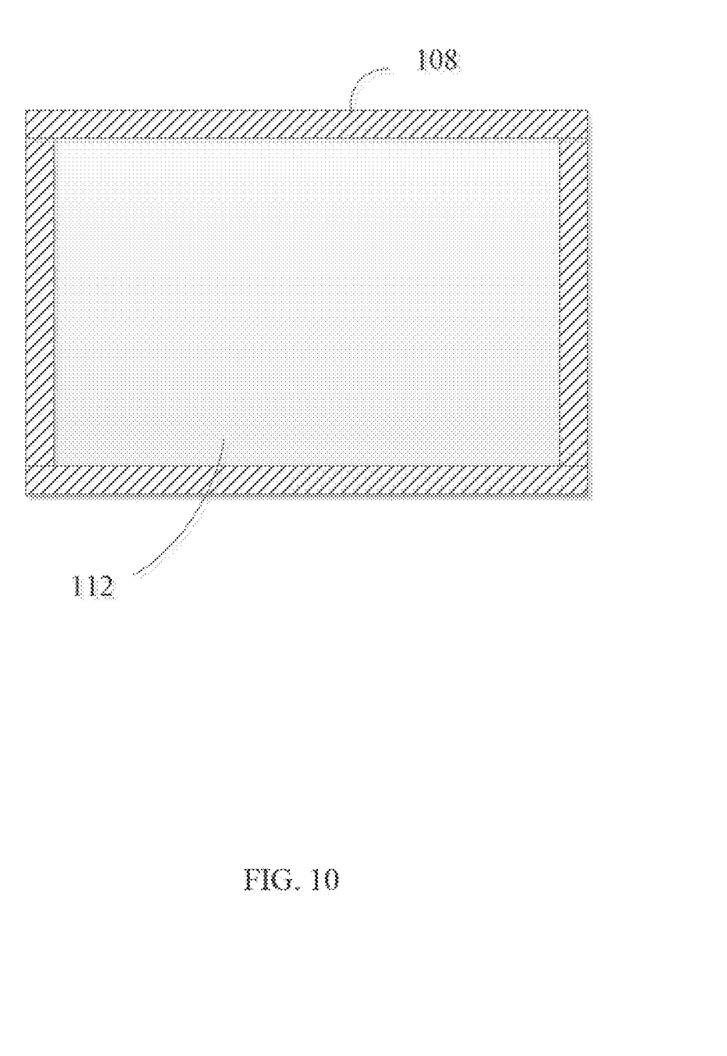
FIG. 10 is a schematic view of an internal structure of the mask with sterilization function in FIG. 9.

Referring to FIGS. 9 and 10, a mask with sterilization function 200 according to a second embodiment is provided. The mask with sterilization function 10 includes a mask body 202, two straps 204, a functional layer 206, a first electrode 208a, a second electrode 208b and a power inlet 210. The functional layer 206 and the two electrodes 208a and 208b are located in the mask body 202, and the two electrodes 208a and 208b are located on a surface of the functional layer 206 and are electrically connected to the power inlet 210. The two electrodes 208a, 208b are used to input current to the functional layer 206 to heat the functional layer 206. The functional layer 206 includes a plurality of micropores, which is a carbon nanotube layer or a carbon fiber layer. The two straps 204 are head mounted.

The first electrode 208a and the second electrode 208b are two linear electrodes, which are respectively located at two ends of the functional layer 206 and are substantially flush with two opposite sides of the functional layer 206. The first electrode 208a and the second electrode 208b are respectively connected to the power inlet 210 through electrode lead wires.

Other characteristics of the mask with sterilization function 200 in the second embodiment are the same as that of the mask with sterilization function 100 in the first embodiment.

Depending on the embodiment, certain blocks/steps of the methods described may be removed, others may be added, and the sequence of blocks may be altered. It is also to be understood that the description and the claims drawn to a method may comprise some indication in reference to certain blocks/steps. However, the indication used is only to be viewed for identification purposes and not as a suggestion as to an order for the blocks/steps. The embodiments shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size, and arrangement of the parts within the principles of the present disclosure, up to and including the full extent established by the broad general meaning of the terms used in the claims. It will therefore be appreciated that the embodiments described above may be modified within the scope of the claims.

What is claimed is:

1. A mask with sterilization function comprising:
two straps, a mask body, a functional layer, a first electrode, a second electrode, and a power inlet; wherein the functional layer, the first electrode and the second electrode located in the mask body, and the first electrode and the second electrode are located on a surface of the functional layer and are electrically connected to the power inlet, the first electrode and the second electrode are configured to input a current to the functional layer to heat the functional layer, the functional layer is a conductive layer and comprises a plurality of micropores, the mask is configured to be worn on a user's face while heating and sterilizing, wherein the functional layer is a carbon nanotube layer comprising at least one carbon nanotube film.

2. The mask of claim 1, wherein the first electrode and the second electrode are cross-finger electrodes.

3. The mask of claim 2, wherein each of the first electrode and the second electrode comprises a plurality of horizontal wires and a plurality of vertical wires, the plurality of vertical wires are crossed with the horizontal wire.

4. The mask of claim 3, wherein the plurality of vertical wires are parallel with each other and spaced apart from each other, and one end of each vertical wire is connected to the horizontal wire, and the other end extend outward from the horizontal wire.

5. The mask of claim 3, wherein the plurality of horizontal wires and the plurality of vertical wires are perpendicular to each other.

6. The mask of claim 3, wherein the plurality of vertical wires of the first electrode and the second electrode are alternately arranged, spaced apart from each other and parallel with each other.

7. The mask of claim 2, wherein ends of the plurality of horizontal wires of the first electrode and the second electrode are electrically connected to the power inlet, and an external power source is energized to the first electrode and the second electrode through the power inlet.

8. The mask of claim 1, wherein the functional layer generates Joule heat when the current flows through the functional layer.

9. The mask of claim 1, wherein diameters of the plurality of micropores are in a range from 1 micrometer to 2.5 micrometers.

10. The mask of claim 1, wherein the carbon nanotube film comprises a plurality of successive and oriented carbon nanotubes joined end-to-end by van der Waals attractive force therebetween.

11. The mask of claim 1, wherein the carbon nanotube film comprises a plurality of successively oriented carbon nanotube segments joined end-to-end by van der Waals attractive force therebetween, and each carbon nanotube segment comprises a plurality of carbon nanotubes substantially parallel to each other, and joined by van der Waals attractive force therebetween.

12. The mask of claim 1, wherein the carbon nanotube film comprises a plurality of carbon nanotubes entangled with each other.

13. The mask of claim 1, wherein the carbon nanotube film comprises a plurality of carbon nanotubes joined by van der Waals attractive force, an angle between a primary alignment direction of the carbon nanotubes and a surface of the carbon nanotube film is ranged from 0 degrees to 15 degrees.

14. The mask of claim 1, wherein when a voltage is input to the functional layer, a current is generated in the functional layer, thereby generating Joule heat and increasing the temperature of the functional layer for sterilization.

* * * * *